United States Patent [19]

Matthews et al.

[11] Patent Number: 4,473,070

[45] Date of Patent: Sep. 25, 1984

[54] INTRAMEDULLARY REAMER

[75] Inventors: Larry S. Matthews; Steven A. Goldstein, both of Ann Arbor, Mich.

[73] Assignee: Regents of the University of Michigan, Ann Arbor, Mich.

[21] Appl. No.: 455,875

[22] Filed: Jan. 5, 1983

[51] Int. Cl.³ .................. A61B 17/32; A61F 5/04
[52] U.S. Cl. ................... 128/92 E; 128/305; 30/352; 408/207; 408/227; 408/713
[58] Field of Search ............. 128/305, 305.1, 310, 128/92 E, 83; 408/713, 204, 207, 227; 30/352

[56] References Cited

U.S. PATENT DOCUMENTS

| | | | |
|---|---|---|---|
| 719,860 | 2/1903 | Platt et al. | 408/713 X |
| 1,063,074 | 5/1913 | Shirer | 408/713 X |
| 1,296,549 | 3/1919 | Mundy et al. | 408/227 |
| 1,662,936 | 3/1928 | Philipp | 408/713 X |
| 1,887,374 | 11/1932 | Emmons | 408/713 X |
| 2,811,187 | 10/1957 | Loam et al. | 408/227 X |
| 3,409,965 | 11/1968 | Fisher | 408/227 X |
| 3,554,192 | 1/1971 | Isberner | 128/83 |
| 3,630,204 | 12/1971 | Fishbein | 128/305 |
| 3,633,583 | 1/1972 | Fishbein | 128/305 |
| 3,702,611 | 11/1972 | Fishbein | 128/305 |

FOREIGN PATENT DOCUMENTS 2822973 11/1978 Fed. Rep. of Germany ...... 128/305

OTHER PUBLICATIONS

Orthopedic Catalog, Richards Mfg. Co., Inc., Memphis, Tenn., 1974, p. 50.
Product Encyclopedia, Zimmer, USA, Warsaw, Indiana, 1978, Kunstscher Instrumentation, Medullary Flexible Reamer, 928-08/17 on p. B57 and Medullary Canal Reamer 401-08/17-p. B58.

Primary Examiner—Ronald L. Frinks
Attorney, Agent, or Firm—Sherman & Shalloway

[57] ABSTRACT

An intramedullary reamer comprising a tapered cylindrical body member, a groove extending along the opposite sides and across the small end of the body member, a plurality of longitudinally disposed valleys disposed in advance of the groove to facilitate removal of cutting chips and a replaceable blade adapted to fit into the groove in the body member, the cutting edge of the blade being exposed above said groove, the open end of the blade being provided with locking means to secure the blade to the body member.

7 Claims, 14 Drawing Figures

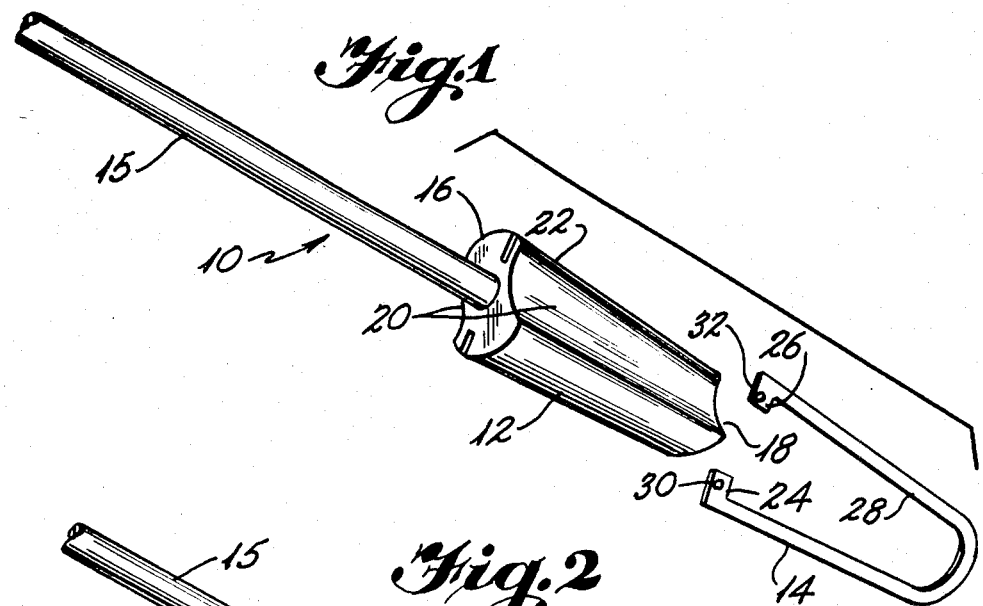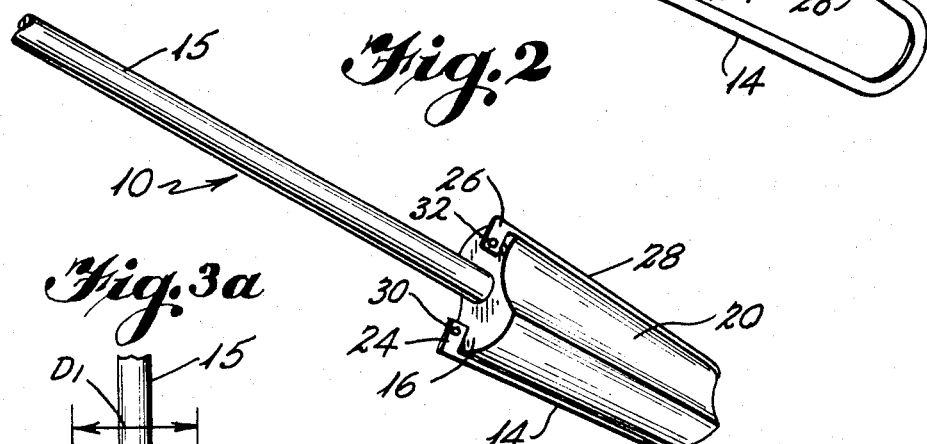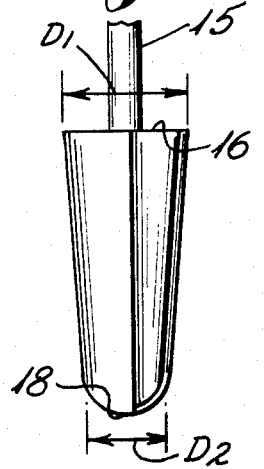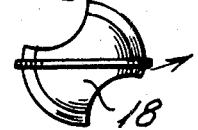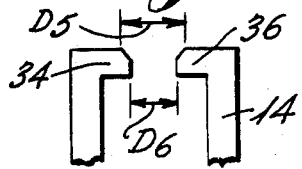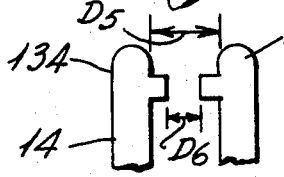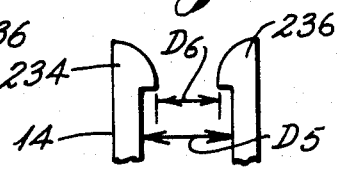

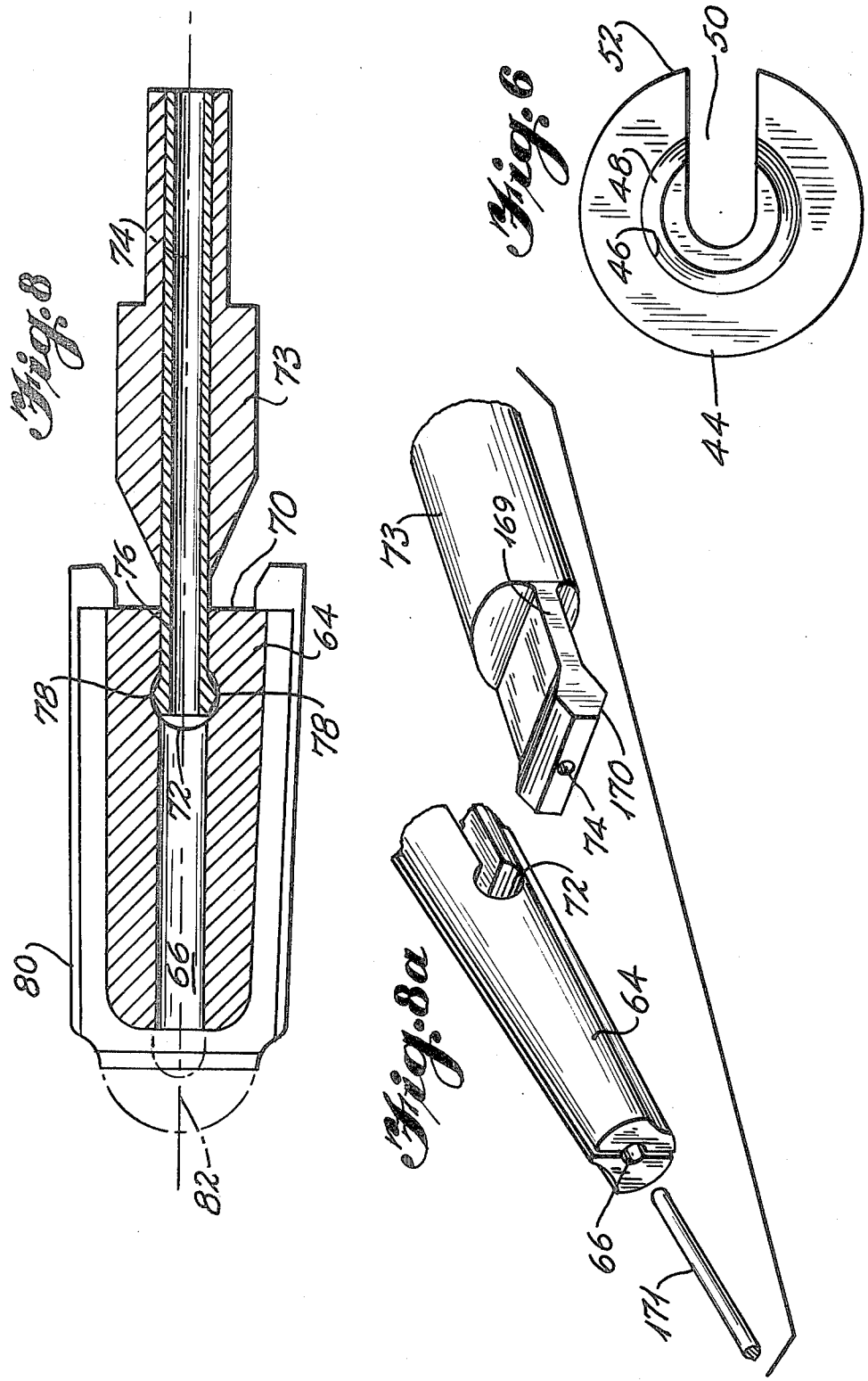

INTRAMEDULLARY REAMER

BACKGROUND OF THE INVENTION

1. Field of the Invention

This invention relates to a surgical rotary bone reamer. More specifically this invention relates to a rotary intramedullary reamer for long bones.

2. Description of the Prior Art

Many fractures of long bones can be stabilized satisfactorily by surgically inserting a shaft, rod or nail down the intramedullary canal of the bone. Since the natural canal is irregular in internal diameter from end to end and since all intramedullary fixation devices gain strength with increases in diameter, most surgical procedures call for incremental reaming. Typically, reamers with 0.5 mm or 1.0 mm increases in outside diameters are used sequentially.

Conventional intramedullary reamers are bullet-shaped, i.e. cylinder with a hemisphere end; and have multiple teeth on their surface. These teeth may be oriented with the long axis of the reamer or at a slight angle thereto. The teeth are generally shallow and give the conventional device the appearance resembling a rotary file. The reamer end may be fixed to a solid shaft or a flexible shaft. The shape of reamers may vary from that described above to that of a sphere or to an acorn shape. Furthermore, the shaft and reamer head may have an axial channel or hole. The shallow teeth produce coarse particulate cutting chips which stay in the valleys between the teeth to clog the reamer head so that it fails to progress. As a result, the reamer must be laboriously cleaned only to be rapidly clogged again.

In addition, in the conventional reamer, the cutting edges cannot be sharpened without altering the outside diameter thereof and therefore ruining the same. To incur less expense, dull ineffective reamers are often retained and used.

Some conventional reamers are not well guided by the wall of the intramedullary canal of long bones and can cut through the wall of the bones.

U.S. Pat. No. 3,633,583 discloses a surgical rotary bone cutter having substantially the shape of a hemisphere and a diametrical slot into which a single flat blade can be positioned. A channel for conveying cutting from the shearing edges is formed in the head alongside each shear edge.

U.S. Pat. No. 3,409,965 describes a tipped cutting tool having a cylindrical body and a ball end provided with diametrical slots. A strip of cutting material is formed into U shape and brazed in the slot to form cutting edges at opposite sides and across the end of the body.

U.S. Pat. No. 1,296,549 discloses a cutting tool comprising a body member with its lateral and forward edges provided with grooves formed in the opposite edges thereof and cutting tips filling said grooves.

U.S. Pat. Nos. 3,630,204 and 3,702,611 disclose surgical reamers having a hemispherical head. Both reamers are designed for forming a hemispherical socket in a bone, e.g. in hip surgery.

U.S. Pat. No. 2,811,187 teaches a dovetail counter-sinking tool in which the tool shaft has a slot in which are secured a pair of pivotal blades.

U.S. Pat. No. 3,554,192 discloses a medullary space drill having a flexible shaft. A drill head is welded and soldered to one end of the shaft whereas the other end is connected to a rotary driver means. The shaft comprises a plurality of parallel flexible elements which are arranged to provide a central passage for receiving an elongated guide element.

None of the above-listed patents discloses a reamer which has a replaceable blade similar to that of the instant invention.

SUMMARY OF THE INVENTION

The present invention provides an intramedullary reamer having a tapered cylindrical body, the smaller end thereof being rounded, and a removable blade. The body is provided with a plurality of valleys for removing cutting chips and a groove which extends outside the valleys and along the opposite sides and across the small end of the body. The removable blade is generally U-shaped and is adapted to fit into the groove in the body, with the cutting edge of the blade being exposed above the groove. The open end of the blade is provided with locking means to secure the blade to the body.

A tool for removing the blade from the body is also provided. The tool comprises a cylinder having a longitudinal slot extending from the surface to the center of the cylinder. One or both ends of the cylinder are provided with a truncated cone portion for spreading the open end of the replaceable blade to facilitate simple removal of the blade from the tapered cylindrical body.

By providing an elongated and tapered body, more of the blade becomes available for cutting than in conventional reamers. The valleys permit removal of the cutting chips to avoid frequent stopping and cleaning of the reamer. Since the blade can be readily exchanged, the problems associated with using a dull blade have been obviated. As a result a more accurate final cut can be obtained.

BRIEF DESCRIPTION OF THE DRAWINGS

FIG. 1 is an exploded view of the present intramedullary reamer.

FIG. 2 shows an assembled intramedullary reamer of the present invention.

FIG. 3A shows a cross-sectional view of the tapered cylindrical body of the present invention.

FIG. 3B shows the end view of the tapered cylindrical body with the blade removed.

FIG. 3C shows the end view of the tapered cylindrical body with the blade mounted thereon.

FIG. 4A shows the construction of one embodiment of the open end of the U-shaped blade of the present invention.

FIG. 4B shows the construction of another embodiment of the open end of the U-shaped blade of the present invention.

FIG. 4C shows the construction of another embodiment of the open end of the U-shaped blade of the present invention.

FIG. 6 shows an end view of the blade remover of FIG. 5.

FIG. 8 shows still another embodiment of the present invention wherein the cylindrical body is cannulated.

DETAILED DESCRIPTION OF THE PREFERRED EMBODIMENT

Figure 5:
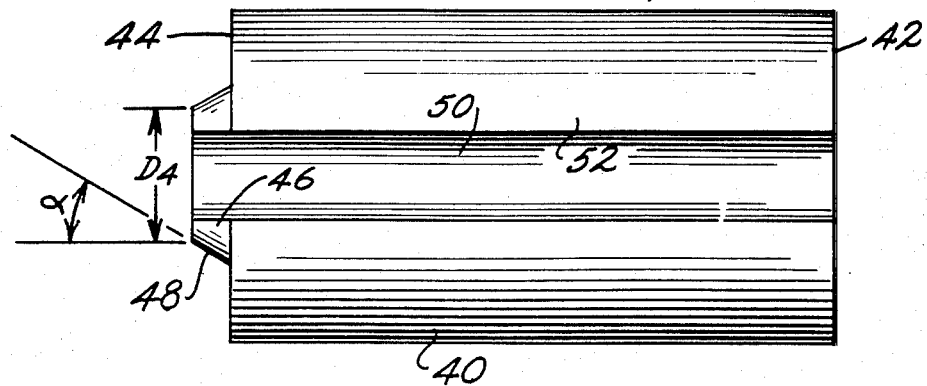
FIG. 5 illustrates a cross-sectional view of the blade remover of the present invention.

According to the present invention there is provided an intramedullary reamer having a replaceable blade and a body portion equipped with a plurality of valleys for the removal of cutting chips. As a result, an improved reamer capable of making good progress in reaming long bones is obtained. Since the blade is readily replaceable, the reaming procedure is further improved to avoid use of dull blades. A tool for quick removal of the blade is also provided.

With reference to FIG. 1, the present intramedullary reamer 10 comprises a tapered cylindrical body 12 and a replaceable blade 14. Shaft 15 is press fitted to tapered cylindrical body 16 or both shaft and body can be integrally formed. Body 12 has a flat end 16 having a larger diameter ($D_1$) and a rounded end 18 having a smaller diameter ($D_2$), as shown in FIG. 3A. In general, $D_1$ is greater than $D_2$ by 0.5 to 2.0 mm. Provided on body 12 are two valleys 20 which extend along the longitudinal axis of body 12. The depth of valleys 20 can be varied. However, valleys 20 should not be too deep so as not to affect the strength of body 12. Usually, the depth of valley 20 at flat end 16, designated to be $D_3$, (FIG. 3B) is from about 10 to about 30% of $D_1$.

Also provided in body 12 is a longitudinal groove 22 extending along the opposite side and across the small end 18 of body 21. Groove 22 is disposed in close proximity to the trailing shoulder of valley 20 as the reamer is rotated in the direction shown in FIG. 3B, i.e. valley 20 is immediately in advance of 22 in the rotational direction of the reamer. The groove has a depth sufficient to store U-shaped blade 14 with the cutting edge being exposed when the entire reamer has been assembled (FIG. 2). The replaceable blade is integrally formed and comprises a right leg and a left leg joined together by a connecting portion. Each of the legs is provided near or at the open end of the blade with means for locking the blade to the tapered cylindrical body. In the embodiment shown in FIG. 1, replaceable blade 14 has a general configuration resembling the letter "U". As one skilled in the art will readily appreciate, the replaceable blade may have a configuration other than U-shaped, e.g. V-shaped. In general, the configuration of the replaceable blade conforms with the shape of the tapered cylinderical body. In FIG. 1, the open end of replaceable blade 14 is provided with projections 24 and 26 which extend perpendicularly into the open end to provide locking means to secure the blade to body 12. Blade 14 is secured to body 12 since projections 24 and 26 rest on flat end 16. The resiliency in the replaceable blade forces the blade to press inwardly towards the longitudinal axis of the body 12. Each of projections 24 and 26 is provided with hole 30 and 32, respectively. These holes are for the insertion of pins in a pair of reverse acting pliers which can be used to separate or spread the open end of blade 14 so that projections 24 and 26 no longer abut flat end 16, thus freeing blade 14.

In another embodiment, the opposing outer corners of projections 34 and 36 are truncated, as shown in FIG. 4A. Such a blade is adapted for application with the blade remover, shown in FIGS. 5 and 6, which consitiutes part of the present invention.

In another embodiment, the opposing outer corners of projections 134 and 136 are contoured as shown in FIG. 4B. Such a blade is adapted for application with the blade remover, shown in FIGS. 5 and 6, which constitutes part of the present invention.

In another embodiment, the opposing outer corners of projections 234 and 236 are radiused as shown in FIG. 4C. Such a blade is adapted for application with the blade remover, shown in FIGS. 5 and 6, which constitutes part of the present invention.

Figure 7:
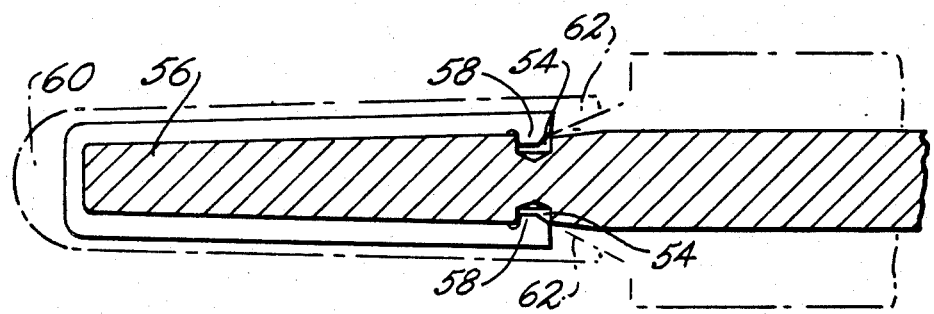
FIG. 7 shows another embodiment of the present invention.

In still another embodiment, the projections in the open end of the replaceable blade extend into holes provided in the tapered cylindrical body instead of resting against flat end surface 16. As shown in FIG. 7, a pair of holes 54 are provided in tapered cylindrical body 56. Projections 58 at the open end of replaceable blade 60 extend into holes 54 to secure the blade in a locked position. The opposing corners 62 of the open end of blade 60 are truncated to provide inclines which act with the truncated cone to facilitate easy removing of the blade from the body. As mentioned above, the projections 58 do not abut or rest against the end surface of tapered cylindrical body 56. As a result, tapered cylindrical body 56 may be a solid shaft which can be coupled directly to a rotary driver means.

With reference to FIG. 5, the blade remover 38 comprises cylinder portion 40 having end surfaces 42 and 44, respectively. Centrally formed on end surface 44 is truncated cone 46. While only truncated cone 46 is shown on surface 44 in FIG. 5, it is understood that surface 42 can also be provided with a truncated cone having dimensions which are different or the same as those of truncated cone 46. Truncated cone 46 has such dimensions that it is capable of spreading truncated corners 34, 36 of blade 14 (FIG. 4) to allow separation of the blade from body 12. In other words truncated cone 46 has such a diameter that inclined surface 48 can pry locked blade 14 from tapered cylindrical body 12. A slot 50 extends longitudinally along the entire length of cylinder portion 40 and truncated cone 46. (or both truncated cones if two cones are used). Slot 50 extends from the outer surface 52 to the center of cylinder portion 40, as shown in FIG. 6. The width of slot 52 is slightly greater than the diameter of the shaft (not shown) to which reamer 10 is attached. Slanted surface 48 in truncated cone 46 is adapted to contact the truncated corners of projections 34 and 36 to spread the open end of blade 14. As a result of the spreading, projection 34 and 36 no longer abut or rest against flat end 16, thus freeing blade 14 from body 12. The angle $\alpha$ between inclined surface 48 and end surface 44 can be approximately the same as $\alpha'$ in truncated corners 34 and 36 in blade 14.

The intramedullary reamers so far discussed are adapted for use with solid shafts. The present reamer can also be used in connection with cannulated shafts, such an embodiment being shown in FIG. 8. Tapered cylindrical body 64 is formed with a bore 66 along its longitudinal axis. Bore 66 extends through the entire length of body 64. Small end 68 of body 64 is rounded whereas large end 70 has a flat surface. Near flat end 70, a cylindrical hole 72 is provided, the hole extending diametrically across body 64. Cannulated shaft 73 is connected to body 64 by means of a modified dovetail 169. The enlarged lock portion of dovetail 170 is not an inverted triangular shape but approximately a hexagon. Cannulated shaft 73 is connected to body 64 by inserting modified dovetail 169 into the cylindrical hole 72 of the body in a lateral direction. The lateral position is then maintained by insertion of an appropriately sized guide pin 171 into the aligned longitudinal bores 66 and 74 of shaft 73 and body 64. Replaceable blade 80 has generally the same construction as that shown above with the exception that the tip 82 thereof is bent over so that it does not block bore 66. Tip 82 is bent at a 90° angle to the longitudinal axis of body 64 so that tip 82 lies flat against small end 68. The radius of curvature for tip 82 is reduced so that when bent, the outer periphery of the tip does not extend beyond small end 68 of body 64. In addition, the central portion of tip 82 is cut so that, after bending the central portion has an opening which conforms to the contour of bore 66.

As an alternative embodiment of the cannulated reamer, a recess may be provided in the distal end of the tapered cylindrical body so that the bent tip of the replaceable blade is stored within this recess and does not protrude out of the body.

Alternatively, the tip of the replaceable blade may be kinked to avoid blockage of the central bore. The kink matches the general contour of the bore. As is well known, cannulation in the reamer and drive shaft permits the use of a guide pin during the reaming procedure. FIG. 7 shows a kinked blade, although the reamer of FIG. 7 is not cannulated.

Figure 9:
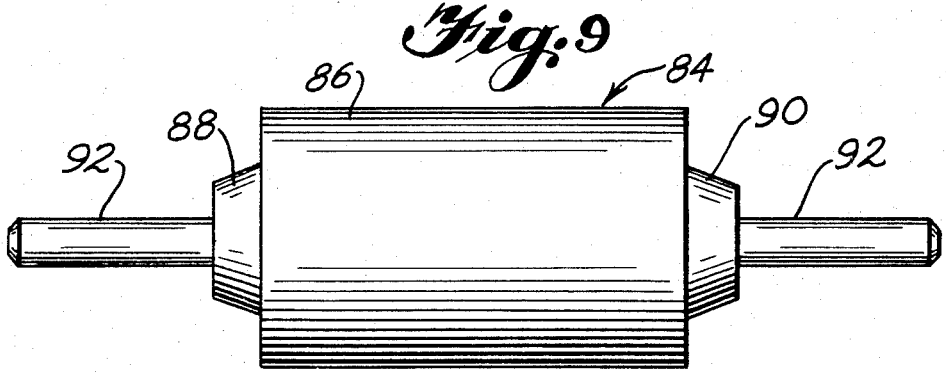
FIG. 9 illustrates a blade remover for the cannulated cylindrical body shown in FIG. 8.

When a cannulated intramedullary reamer is used, it is necessary to modify the present blade removing tool. In a cannulated reamer, the shaft attached to the proximal or large end of the tapered cylindrical body must be first removed. In so doing, handling of the reamer becomes difficult since there is no convenient place to hold the reamer. As a result, the tool remover shown in FIG. 9 has been developed. Modified blade remover 84 (see FIG. 9) comprises a solid cylindrical body 86 having at each end a truncated cone 88 and 90 for spreading the open end of a replaceable blade to permit removal of the blade. Extending along the longitudinal axis of truncated cones 88, 90 and solid body 86 are cylindrical rods 92. To remove a blade, one of rods 92 is inserted into the bore 66 in body 64 and pushed to spread the open end of the replaceable blade to force out the blade. No longitudinal slot is provided in blade remover 84 since the shaft is first disconnected from the reamer body. By providing rods 92 in the blade remover, the blade removal step can be greatly simplified with much less chance of having the surgeon injure himself/herself when changing blades.

In all of the embodiments shown herein, the tapered cylindrical body is provided with a plurality, normally two, valleys for collection and disposal of cutting chips. The valleys are located in advance of the replaceable blade so that as the reamer rotates, cutting chips are pushed into the valley. The replaceable blade is housed in the groove in the tapered body, with the cutting edge being exposed, i.e. extending outside the groove.

The tapered cylindrical body and replaceable blade of the present invention can also be used in conjunction with flexible shafts.

To use the present intramedullary reamer, the largest reamer which easily fits the bone's intramedullary space is selected and attached to a rotary power device which is advanced through the bone's canal. Successively larger reamers are selected and used to rotationally advance reaming until the canal is regular and has the optimal size for the fracture fixation device. Using the reamer of FIG. 2 as an example the blade is inserted into groove 22 and locked in place by fitting projections 24 and 26 over flat end 16 of body 12. The reaming procedure is then conducted. When the blade become dull, the blade can be removed by using a pair of reverse acting pliers to spread the open end of the replaceable blade or the blade remover shown in FIG. 6.

Typically, $D_1$ ranges from about 7 to 20 mm,
$D_2$ ranges from about 6 to 19.5 mm,
$D_3$ ranges from about 0.7 to 6 mm,
$D_4$ ranges from about 3 to 14 mm, and
$D_5$ ranges from about 3.5 to 14.5 mm.

The overall length of the present reamer head is about 25 to 40 mm. Usually, the cutting edge of the replaceable blade projects out of groove 22 by about 0.5 mm. Groove 22 has a depth of about 1 to 3 mm and blade 14 has a width of about 0.5 to 1.5 mm. The projections on the open ends of blade 14 usually have a length of 2 to 4 mm. The intramedullary reamer of this invention can be made of any material useful in the surgical art. The gap $D_6$ between the projections on the open ends of blade 14 typically has a width which ranges from 2 to 14 mm.

What is claimed is:

1. An intramedullary reamer comprising:
   a tapered cylindrical body member having a large end and a small end, the small end being rounded, a groove extending along the opposite sides and across the small end of said body member, a plurality of longitudinally disposed valleys disposed in advance of the groove to facilitate removal of cutting chips, and
   a blade having a right leg and a left leg joined by a connecting portion, the blade being integrally formed and adapted to fit into the groove in the body member, the cutting edge of the blade being exposed above said groove, the open end of said blade being provided with locking means to secure said blade to said body member.

2. The reamer of claim 1 where said blade is replaceable.

3. The reamer of claim 1 wherein the locking means comprises projections which extend from said blade to engage the large end of said body member when said blade is fitted over said body member.

4. The reamer of claim 3 wherein the opposing outer corners of said projections are truncated to facilitate spreading of the open end of said blade for removing said blade from said body member.

5. The reamer of claim 1 additionally comprising a blade removing member which comprises a cylinder portion and a truncated cone member provided on at least one end surface of said cylinder portion, a longitudinally disposed slot extending from the surface of the cylinder portion to the center thereof, said slot extending through said cylinder portion and said truncated cone member.

6. The reamer of claim 1 wherein said blade is U-shaped.

7. The reamer of claim 1 wherein said cylindrical body member is provided with a longitudinal central bore and the distal end portion of said blade is bent so as not to block the opening in the distal end of said cylindrical body member.

* * * * *